United States Patent [19]

Hofmann

[11] 3,949,741
[45] Apr. 13, 1976

[54] WRINKLE-REDUCING METHOD

[76] Inventor: Ross E. Hofmann, 1104 Malaga Ave., Coral Gables, Fla. 33134

[22] Filed: May 15, 1974

[21] Appl. No.: 470,280

[52] U.S. Cl. ............................................. 128/76 B
[51] Int. Cl.² ........................................... A61F 5/08
[58] Field of Search ......... 128/76 B, 76 R, 156, 163

[56] References Cited
UNITED STATES PATENTS

| | | | |
|---|---|---|---|
| 2,001,862 | 5/1935 | Battey | 128/76 B |
| 2,540,247 | 2/1951 | Dillon | 128/76 B |
| 3,068,863 | 12/1962 | Bowman | 128/163 X |
| 3,092,103 | 6/1963 | Mower | 128/163 X |
| 3,483,018 | 12/1969 | Waldman | 128/156 X |
| 3,635,755 | 1/1972 | Balinth | 128/156 X |
| 3,645,835 | 2/1972 | Hodgson | 128/156 X |
| 3,763,858 | 10/1973 | Buese | 128/156 |
| 3,769,071 | 10/1973 | Trancik | 128/156 X |

*Primary Examiner*—John D. Yasko
*Attorney, Agent, or Firm*—Cushman, Darby & Cushman

[57] ABSTRACT

A method and appliance for reducing facial wrinkles. In the method, a pressure-sensitive adhesive appliance is tightly applying to wrinkle prone areas of the human face in such a manner that the skin under the appliance is placed in a flattened and smoothed configuration. The appliance remains in place for at least four hours and then is removed in a manner to strip dead skin cells from the skin. These steps are repeated a plurality of times over a long period of time.

The appliance transmits moisture at least equal to that transmitted by facial skin of a human and is comprised of a film and a pressure-sensitive adhesive coating. The film has a tensile strength and an ultimate elongation consistent with flattening and smoothening the skin. The adhesion between the adhesive and the film is greater than the adhesion between the adhesive and the skin.

11 Claims, 6 Drawing Figures

WRINKLE-REDUCING METHOD

The present invention relates to a method of reducing wrinkles, especially wrinkles on the human face and to specialized appliances for use therewith. More particularly, the invention relates to a method and specialized tape for use therewith wherein the application of the tape causes a configuration of the skin and conditions which are conducive to wrinkle removal.

BACKGROUND OF THE INVENTION

As is well appreciated, human skin begins to form planar discontinuities, commonly-called wrinkles, by the time that the human reaches maturity, and often even therebefore. As the human grows older, these wrinkles can produce an unsightly facial appearance. The art has expended much effort in attempts to prevent wrinkle-formation and/or to reduce the severity of already-formed wrinkles. These efforts have taken a variety of forms, including creams, salves, vapor treatments, mud packs, medicants and massage exercises.

In yet another form of the effort in the art, it has been proposed that certain mechanical appliances may be used to apply stresses to the skin for wrinkle removal. A wide variety of such mechanical devices has been proposed in the art, but the major emphasis of these mechanical devices has been that of effecting a stretching of the skin while the devices are in place and, thereby, assertedly mitigating the wrinkles. Illustrative of these approaches are U.S. Pat. Nos. 2,296,903; 2,207,730; and 2,392,377. However, the effectiveness of these mechanical devices has been repeatedly questioned. Further, such mechanical devices are difficult to apply to the skin and can only be worn with discomfort. In an effort to make these appliances more easily applied to the skin and more comfortable, it has also been proposed that the devices be held in place by pressure-sensitive tape. But even with this improvement, the devices are still difficult to apply.

In the same vein as the mechanical devices, the art has suggested skin-gripping compositions, such as court plaster (se U.S. Pat. No. 2,540,247). Alternately, fabric can be coated with an adhesive, such as gum arabic, and applied to the skin for longer periods. It is asserted that the fabric will flatten the tissue and cause mitigation of the wrinkles. The function proposed by these approaches is to distort the wrinkled tissue and cause mitigation thereof.

Thus, in summary, the art has suggested various devices for wrinkle mitigation, which devices, either by mechanical or adhesive action, are said to hold the skin in a condition which will mitigate wrinkles. Unfortunately, these approaches in the art fail to account for certain anatomical characteristics of the skin, and, therefore, are not capable of dealing with the major cause of wrinkles.

The skin or integument is stratified into two main layers. The epidermis is the surface layer; the corium or dermis is the inner layer. This inner layer (corium) is the connective tissue that blends into the subcutaneous tissue below. The epidermis is composed of a many-layered cellular membrane, while the corium is a dense, connective tissue layer, mostly, non-cellular. The subcutaneous tissue, on the other hand, is a thick layer which stores fat and acts as a cushion over the body frame of bone and muscle. Facial skin, as well as skin on other parts of the body, has systematically arranged contours reflecting the underlying arrangement of fibers in the deep dermis. These contours or cleavages are termed Langer's skin tension lines and have been mapped for every region of the body. On the face, these lines follow a characteristic form. Wrinkles occur in a characteristic pattern as evidenced by these lines of cleavage, as well as from folds or creases perpendicular to the long axis of certain facial muscles. The present invention is based on the discovery of a method and appliance for use therewith which can minimize the wrinkling effects of cleavages and folds, and correspondingly, reduce wrinkles.

OBJECTS OF THE INVENTION

It is, therefore, an object of the invention to provide a method of reducing facial wrinkles.

It is a further object of the invention to provide a method which can be used without specialized skills, and, therefore, allow the method to be practiced by the user himself. It is yet a further object of the invention to provide such method wherein the method is relatively inexpensive and can be easily within the financial means of nearly all users. Other objects will be apparent from the following disclosure and claims.

BRIEF DESCRIPTION OF THE INVENTION

A basic understanding of the various layers and strata within each layer of the skin (integument) and the formation and movement of cells within these strata, as revealed by electron microscope studies, is necessary for an understanding of this invention.

The deeper layer of the skin, the dermis or corium, is a dense connective tissue richly supplied with blood vessels, nerves, and associated sensory organs. The bottom layer of the dermis, the reticular layer, contains few cells, and is a dense network of collagenous fibers continuous with the fatty subcutaneous tissue below. The top layer, the soft papillary layer, contacts the lowest layer of the epidermis above, has more cells, and is thrown into folds and projections interdigitating with local thickenings of the lowest stratum of the epidermis.

The epidermis, or upper skin layer, is epithelium of the stratified squamous variety, consisting of several layers of cells, and six principal strata from bottom to top. The cells that lie in the deeper strata proliferate actively and the daughter cells are passed gradually toward the surface, undergoing cornification as they approach the surface and are finally lost by desquamation. The basal cells are cylindrical and oriented perpendicular to the surface of the skin. The daughter cells gradually transform as they move upward, becoming flattened and cornified at the outermost strata (stratum corneum and stratum disjunctum) of the skin. The cell contents transform almost entirely into keratin and the outer layers of cells are progressively cast off as new cells arrive from below. The cells stay only a short while as horny cells in the stratum corium before being sloughed-off on the stratum disjunctum. About 2 to 6 weeks are required for a basal cell to complete its life cycle before being shed at the surface of the skin, depending on age, skin condition, environment, etc. The epidermis is, therefore, constantly renewing itself in that cells die in the journey to the surface of the skin at about the same rate that the cells are divided in the skin below.

The skin has several different kinds of cutaneous contours arranged systematically. They tend to mirror the underlying arrangement of elastic and collagenous fibers in the deep dermis. As the skin ages, these lines or contours are exaggerated. Termed Langer's skin tension lines, they have been mapped for every section of the body. Surgeons have learned that these are cleavage lines and the underlying fibers are parallel to these cleavage lines. Thus, incisions aligned with the cleavage lines have greater retraction as the fibers and cell movement close more evenly.

Wrinkles on the face are connected both to the muscles of facial expression, as well as the bundles of dermal collagen that create Langer's skin tension lines. Contraction of the muscles originating or inserted in the deep dermis throws facial skin into folds or creases perpendicular to the long axis of the muscles, in some areas following the pattern of Langer's lines, in other areas deviating from these.

Central to the present invention is the placing of a particular appliance tightly on the skin whereby the skin is flattened, rather than stretched from some external appliance, as according to the prior art, and in this process the appliance influences the pattern of epithelium growth and desquamation as noted above, and thereby serves to lessen the tendency of wrinkle formation in the lines of cleavage characterized by Langer's lines and in the folds influenced by muscles. The action of the appliance is to keep the layers of the cells of the epidermis in a smooth configuration, through a combination of pressure and flattening, and to thereby influence the shape and pattern of the cells as they develop. In other words, the process and appliance cause the renewing cells to fill in the cleavage lines and mitigate the skin creases and this results in a reduction of the formation of wrinkles.

As a further aspect, the appliance at least partially immobilized the wrinkle prone area and thereby mitigates skin creases caused by facial expressions. Thus, squinting, frowning, brow wrinkling, etc. accummulate the effect on the natural cleavage lines and folds and corresponding increase the number and severity of wrinkles. Facial expressions are particularly difficult to control in persons with certain psychological characteristics and these expressions are responses to subconscious mental activity, e.g., tension, intensity of feeling, etc. These facial expressions, however, significantly increase the problem of wrinkles.

The appliance also functions to remove cells from the epidermis and thereby accelerate the renewal of the skin by action of the cells more rapidly moving outwardly. This rapid renewal of the cells and the configuration imposed upon the skin by the appliance produces a total effect of mitigating and removing wrinkles.

Thus, there are three major features to the present invention: a specialized appliance which may be easily applied and removed from the skin; the placement of that appliance in such a manner as to both smooth and flatten the skin thereunder; and the ability of the appliance and method to accelerate the renewal of cells in the epidermis. Other less central features of the invention are explained below.

The appliance is in the form of a yieldable, and preferably clear, moisture transmitting film with physical properties sufficient to provide the desired smoothening and flattening effect of the skin. Suitably, the film is a polymeric film. The film is applied to and held on the skin by an adhesive (preferably at least a semi-clear adhesive). The renewal of the cells at the epidermis is accelerated by the method of use of the appliance and/or by the nature of the adhesive. In one aspect of the foregoing, daily removal of thee adhered appliance will also remove the more loosely connected dead cells at the surface of the epidermis and thereby accelerate the movement of renewed cells from the inner layers of the skin to the surface of the epidermis. Alternately, or in addition thereto, the adhesive may contain cell loosening agents, such as very mild acids, which promote loosening of the dead cells at the surface of the epidermis and facilitates the cell removal by the adhesive.

As can be appreciated from the above, the physical properties of the film and adhesive are most important. The adhesive must be capable of tightly holding the applied film to the skin for extended periods of time. Further, since adhesives which require extended times to develop the adhesion, e.g., drying of glues and the like, would not be satisfactory for the obvious reasons, the adhesive should be a pressure-sensitive adhesive. This also allows the film to adhere to the skin while being pressed in the correct configuration to flatten and smooth the skin. Also, the adhesive must preferentially adhere to the film than to the skin so that the film/adhesive may be totally stripped from the skin without leaving any significant amounts of adhesive thereon.

The film must also have the ability to be adhered by the adhesive, and therefore, must have surface properties consistent with that requirement. The film must also have the physical properties to provide the required flattening and smoothening of the skin for substantial periods of time without significant "creep" or elongation which would deplete those desired effects. Similarly, the film must have sufficient tensile strength to fully strip from the skin. The film must also transmit moisture. For a cosmetic appearance sake, it is preferable for the film to be transparent, or nearly so, and/or to have a surface appearance approaching that of the skin.

The film/adhesive combination, therefore, is preferably in the form of a special pressure-sensitive tape of the above-described characteristics. Such a tape allows ease of application, removal and reapplication. Of course, a new piece of tape is used for each reapplication.

Thus, in a preferred form of the method of the invention, a pressure-sensitive adhesive appliance is tightly applied to wrinkle prone areas of human skin, e.g., the face, in such a manner that the skin under the appliance is placed in a flattened and smoothed configuration. The appliance is allowed to remain in place for a significant time, i.e., at least four hours, so that this configuration of the skin can provide the effects discussed above. Thereafter, the appliance is removed and this removal, thereby, strips dead skin cells from the surface of the skin. The application of the appliance of the invention (by a new piece of the appliance), the remaining in place for at least four hours, and the subsequent removal of the appliance is repeated a plurality of times, but no more than 48 hours should elapse between any repetition thereof, or otherwise, the effect will be essentially lost. Also, repetitions of the application/removal are continued for at least 15 days or the effect is essentially lost. The appliance must be capable of transmitting an amount of moisture at least equal to the moisture transmitted by the normal facial skin of a human at rest. Otherwise, excess moisture would collect under the appliance and cause loss of adhesion to the skin, thus defeating the purpose of application of the appliance. The appliance is preferably composed of a relatively clear film, and a pressure-sensitive adhesive, preferably at least a semi-clear adhesive, coating thereon. In order to provide the flattening and smoothening of the skin, the film must have requisite tensile and elongation properties. The tensile strength of the film must be at least 3 pounds per inch and have an elongation of between 20 and 150%. The pressure-sensitive adhesive must provide an adhesion of between 5 and 50 ounces per inch between the adhesive and the film and between 2 and 30 ounces per inch between the adhesive and the skin and the adhesion between the adhesive and the film must be greater than the adhesion between the adhesive and the skin.

DETAILED DESCRIPTION OF THE INVENTION

For purposes of the present specification and claims, the term "wrinkle prone area of the human face" defines those areas wherein substantial numbers of lines of cleavage characterized by Langer's skin tension lines, as well as folds or creases in the skin created by muscle action, are present and wherein wrinkles in human facial skin are produced to the extent that the wrinkles are visible from a conversation distance. These areas will include the bridge of the nose, the outside corners of the eyes (sometimes referred to as crow's feet), the corners of the mouth, and the forehead, among other areas. As can be easily appreciated, the appliance and method of the present invention is equally applicable to all areas of the body, but for purposes of the regimen required for the present invention, the method would normally be practiced only in those areas which develop sufficient wrinkles to be psychologically impairing.

There are a number of features of the present invention which must be observed in order to obtain the benefit of the invention, both in connection with the method and in connection with the appliance by which the method is practiced. Concerning first the major featues of the method, it is necessary that the wrinkle prone area be depressed in such a manner that the skin thereunder is flattened and smoothed. Thus, by placing the skin in a more planar configuration, the cleavage lines are so distorted that renewed cells moving from the inner to the outer layers of the skin will not be preferentially diverted from those lines of cleavage, but will have, essentially, an equal opportunity to be disposed in those, otherwise, lines of cleavage. Further, the folds perpendicular to the longitudinal axes of the muscles are prevented, thus mitigating their effect in creating permanent skin creases. This avoids the natural tendency of wrinkles, produced by these lines of cleavage and folds in the skin. Simply stretching the skin, as was thought to be necessary in the prior art, will not accomplish the present invention. The skin must be held in this somewhat planar configuration, i.e., flattened and smoothened in order for the present invention to work.

To accomplish the above end, the appliance, consisting essentially of the pressure-sensitive adhesive and the film of the required properties, can be applied by pressure to the skin and lock the skin in the rather planar configuration of the film of the appliance. In other words, the broad area of the appliance will bridge many lines of cleavage and folds. Since the skin is locked to the film by the adhesive, including the cleavage and fold lines, and since the film is of such area and physical properties that it will not be deflected toward the skin, but maintain its planar configuration, the lines of cleavage and folds will be held in a more planar configuration by adherence to the film.

Figure 1:
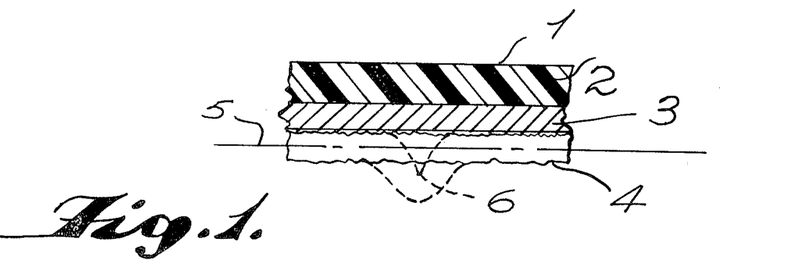
FIG. 1 is a cross-sectional view of a preferred form of the present appliance and shows in diagrammatic form a function of the invention.

The foregoing is diagrammatically illustrated in FIG. 1 where the appliance, generally, 1, is composed of a plastic film 2 and an adhesive 3 coated thereon. The area of the skin to which the appliance is applied is indicated by 4. It will be seen, as shown in FIG. 1, that while the appliance is in place the skin is in a generally planar configuration, as indicated by the center-line 5. However, prior to application of the appliance the skin had wrinkles therein, at cleavage and crease lines, indicated by the configuration of dotted portions 6. When the appliance is pressed tightly onto that area, the adhesive locks into the wrinkle, as well as other portions of the skin. When pressure is released, after the appliance is tightly adhered to the skin, the adhesive draws the wrinkle upwardly toward the appliance, by virtue of the tight adhesion, and tends to flatten the wrinkle into a more planar or smooth configuration.

From the foregoing it can be understood that the properties of the film and of the adhesive are quite critical to success of the invention. It can also be understood that the invention primarily centers around a pressure application of the appliance to flatten and smooth the skin so that the wrinkles are more planarly configured, for the purposes noted above.

Of course, a rather momentary flattening of and smoothening of the wrinkles will not provide sufficient time for significant amounts of cells to fill in the cleavage lines and folds or creases, as discussed above. Accordingly, for the invention to have reasonable amounts of success, the appliance must be left in place for some time. Generally speaking, the appliance must be left in place for at least four hours at a time and more preferably, at least six to eight hours at a time. Thus, for example, leaving the appliance in place overnight would be satisfactory for purposes of the present invention. This will provide sufficient time for substantial numbers of cells to fill in the cleavage lines.

Since the rate at which the cells move outwardly from the inner to the outward portions of the skin is accelerated when the outer dead cells are sloughed off at a greater rate, another important feature of the invention is the periodic removal of the appliance. This periodic removal strips the dead skin cells from the surface of the skin and thereby accelerates this desired process. For this reason, it is very important in the present invention that the adhesion between the adhesive and the film be greater than the adhesion between the adhesive and the skin. Otherwise, when removing the appliance, the adhesive, at least in part, could remain on the skin and not provide this desired stripping of dead skin cells. Also, the adhesive is preferably removed from the skin for aesthetic purposes, although this is not the central idea of requiring this relative degree of adhesion.

For the foregoing reasons, as part of the present invention, it has been discovered that the application/removal/reapplication of the appliance in a periodic manner so accelerates removal of the dead cells and correspondingly accelerates renewal of cells that substantial benefits are provided in filling the cleavage lines with renewed cells. Thus, the application and removal of the appliance should be repeated a plurality of times, with repeats thereof not being more than 36 hours apart. Otherwise, the rate of this additional removal of dead skin cells will not be sufficiently great to provide substantial benefits. Of course, less time between repeats of application and removal of the appliance is preferred. Therefore, it is preferred that the appliance be applied and removed at least once every 24 hours. On the other hand, since the appliance should stay on for a minimum of four hours at a time, the repeats should not be closer than every four hours.

Also, in connection with the foregoing, the repeated application and removal of the appliance must be continued for some significant length of time in order to obtain benefits of the invention. Thus, the repeats should be continued for at least 15 days in order to provide sufficient time for renewed cells to fill in the cleavage lines and mitigate the wrinkles. However, even 20 to 30 days would not normally complete the process and substantial additional time for repetition of the application/removal of the appliance will usually be required. This additional time will depend upon the age of the user, (which, of course, influences the rate of cell renewal), the condition of the skin of the user, the care with which the appliance is applied, the hours elapsing between repetition of application/removal of the appliance, and the like. Thus, for many users, 60 days or more may be required before minimum satisfactory results are obtained. On the other hand, three months or even up to six months may be required for users with extreme difficulties of wrinkles in the skin. The effects of the invention are gradual in nature and changes in wrinkles between relatively short times, i.e., a few days, will be slight.

It should also be appreciated that the effects of cleavage lines and muscle creases in the skin will continue and after discontinuance of the present method, these cleavage lines and creases will again tend to produce wrinkles. Therefore, after the wrinkles are removed, at least some application of the method should be continued to retain the effects thereon. Preferably, the method of the invention is continued indefinitely, in order to fully ensure that the effects of the invention are retained. However, in this continued application, the criticality of the method becomes less demanding for reasonable results.

In regard to the important features of the invention concerning the appliance, per se, of course, the appliance must be capable of performing of the steps of the method, as described above. Central to this method is the ability of the adhesive of the appliance to provide the flattened and smoothed configuration of the skin when the appliance is properly in place. Many combinations of film and adhesive may be capable of providing that result for a limited time, but unless the appliance has the present requisite moisture transmission properties, that required adhesion will be rapidly lost due to moisture accumulating under the appliance and breaking the required adhesion between the adhesive and the skin. As is well known, the skin continuously gives off moisture, both in the form of vapor and liquid. If the appliance is not capable of transmitting the amount of moisture passed through the skin, then that moisture will begin to collect under the appliance, and in a relatively short time, the adhesion between adhesive and the skin (thus, the appliance) will rapidly deteriorate and will not be sufficient to maintain the wrinkle in the planar configuration required. The appliance, of course, may well stay in place, but the appliance will not be capable of maintaining the wrinkle in the required planar configuration. For these reasons, the total appliance, including the film and the adhesive must be capable of transmitting an amount of moisture from the skin through the appliance (to dispose thereof to the atmosphere) which is at least equal to the moisture transmitted by normal facial skin of the human at rest. Preferably, of course, this moisture transmission should be greater than the moisture produced by the facial skin of a human at rest and should be capable of transmitting moisture produced by facial skin of a human with at least light physical activity. Thus, it is preferred that the moisture transmission rate be at least 0.5 milligrams per square foot per second and more preferably, at least 1.0 milligrams per square foot per second. Of course, higher rates are preferred, e.g., 1.5 or 2 milligrams per square foot per second or greater.

Also, since the film must provide physical properties sufficient to hold the wrinkles in a planar configuration, the film should have minimum tensile strengths and ultimate elongations such that the rigidity of the film is sufficient to accomplish that desired result. On the other hand, the film should be sufficiently flexible that it can be configured to the exact shape of the face of the user in order that the desired results be obtained. Thus, the film should have a tensile strength of at least 3 pounds per inch and more preferably, at least 7 pounds per inch. Likewise, the ultimate elongation should be between about 20 and 150%, more preferably, between about 40 and 100%. Within these ranges, the film will provide the requisite physical properties to accomplish the desired result.

The adhesive is quite critical to the success of the invention. As noted above, in order that the skin may be first flattened and smoothened, the appliance must be applied with pressure, generally normal to the wrinkle itself. For this reason, it is also desired that the adhesive be a pressure-sensitive adhesive so that the adhesive can be adhered to the skin and wrinkle during this pressing of the appliance thereon to. Further, once the appliance is in place, the adhesive must have sufficient adhesion between itself and the film so as to not be delaminate from the film by reason of the retracting urging of the wrinkle. Similarly, there must be sufficient adhesion between the skin and the adhesive that the wrinkle is not able to retract from the adhesive. On the other hand, since when the appliance is removed it should strip dead skin cells, the adhesive must be capable of being pulled from the skin in the stripping operation. Therefore, the adhesive must have greater adhesion to the film than to the skin. For satisfactory operation, the pressure-sensitive adhesive should provide an adhesion of between 5 and 50 ounces per inch between the adhesive and the film and about 2 and 30 ounces per inch between the adhesive and the skin, and as noted above, the adhesion between the adhesive and the film must be greater than the adhesion between the adhesive and the skin.

Also, in order to be effective for the present purposes, the appliance must be so configured that it can be received by the wrinkle prone areas of the skin in such a manner that effective pressure can be exerted when applying the appliance to accomplish the flattened and smoothened required configuration of the skin. If the appliance is not properly shaped, then application would be too difficult for effective results. For example, if it were desired to apply the appliance to the forehead and bridge of the nose, excess amounts of the appliance which extend towards the eyesockets and eyebrows would not only be uncomfortable, but would render it most difficult, if not impossible, to apply the present appliance in an effective manner. Thus, without proper configuration of the appliance, the intent and result of the invention will be defeated.

Figure 2:
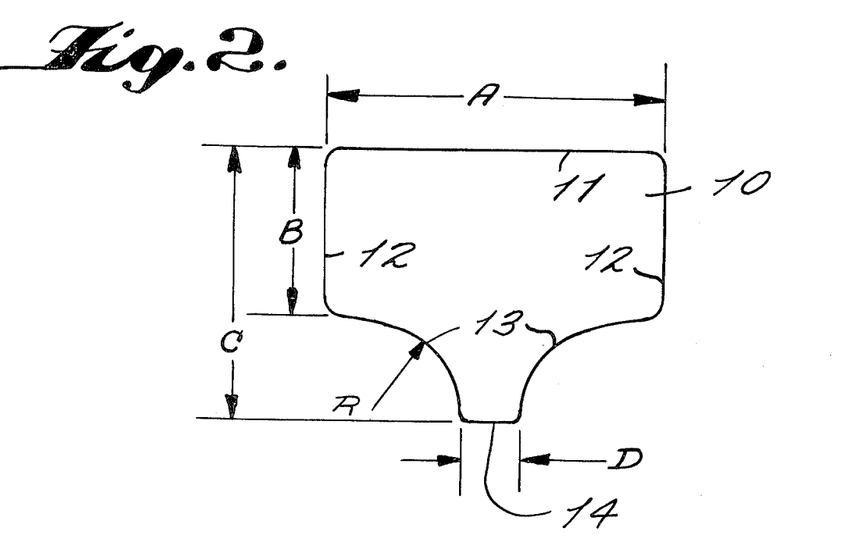
FIG. 2 is a plan view of a configuration of an appliance of FIG. 1 which is particularly suitable for removing wrinkles at the forehead and bridge of the human nose.

As examples of the foregoing, FIG. 2 shows a useful configuration of the appliance for application to forehead and the bridge of the nose. In FIG. 2, the appliance generally 10, has a planar shape wherein an upper edge 11 has a length sufficient to span completely the wrinkle prone area of the skin in the midforehead. This length A can be from about 6.0 to about 9.5 centimeters, but is more usually about 6.5 cm. to 8.0 cm. The configuration also has side edges 12 which are of dimensions B, such that the appliance can extend from above the eyebrow into the area of the forehead a distance sufficient to completely cover that wrinkle prone area. The distance B can be from as little as about 2.5 cm. to as much as about 6.0 cm., but more generally, will be between about 3.0 cm. and 4.5 cm. The appliance also has radius edges 13 (R is between 0.5 cm. and 3.0 cm.) which provide a configuration such that the appliance can be placed between the eyebrows and at or above the bridge of the nose without interfering with either the eyebrows or the eyesockets of the user. The distance C which includes the distance B can be between about 3.5 cm. to about 9.0 cm., but more generally, that distance will be between about 5.0 cm. and 6.5 cm, especially between 5.5 and 6.0 cm. The lower edge 14 of the appliance should have a distance D commensurate with the distance of the bridge of the nose. This is generally between about 0.5 cm. and 1.8 cm., i.e., 0.8 cm. and 1.5 cm. for the tape. This general shape is defined herein as "in the shape of a human forehead."

From the above, it can be seen that configurations of the above nature will allow the appliance to be firmly pressed in the wrinkle prone area of the forehead above the bridge of the nose without such interference from the actual shape of that area as to prevent useful application of the appliance to the face. This kind of configuration is very important to success of the invention.

Figure 3:
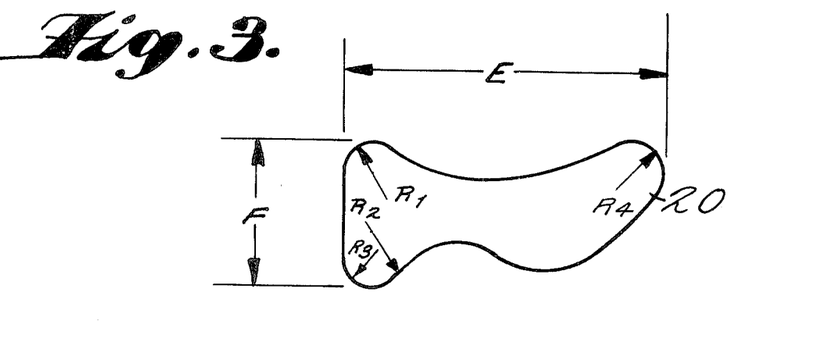
FIG. 3 is a plan view of a configuration of an appliance of FIG. 1 which is particularly suitable for removing wrinkles in the infra orbital region below the human eye and extending to the temple past the outside corner of the eye.

As another illustration of the foregoing, FIG. 3 shows a useful shape of the appliance for applying to the right and left infra orbital areas, below the eyes and into the temples and the outside corners of the eyes. The appliance has a configuration which allows the appliance to be applied to the areas below the eye and extending to the temple, past the outside corner of the eyes in a manner which will span the entire wrinkle prone area, but will not interfere with either the eyebrows or the hairline at the side of the face, which would, essentially, make very difficult or impossible proper application of the appliance. The appliance generally 20, has a length of E of between 5.0 and 8.0 cm., a width F between 3.0 and 4.0 cm. and where $R_1$ and $R_3$ are between 0.5 and 1.0 cm. and $R_2$ is between 0.7 and 1.5 cm. This general shape is defined herein as "in the shape of a human face infra oribital area".

Of course, the appliance can be configured for any particular person and in a planar shape that corresponds to a portion of the human face to which the appliance is to be applied. Thus, one skilled in the art can determine configurations of suitable dimensions. The important point is that the appliance must be appropriately configured so that the appliance can be applied to the particular wrinkle prone area in such a manner that the normal pressure on application will result in the flattened and smoothened configuration of the skin under the appliance. If such configuration of the appliance is not provided it will be most difficult, if not impossible, to position the appliance in that required manner. For this reason, appropriate configurations of the appliance are most important to the success of the invention.

Figures 4, 5:
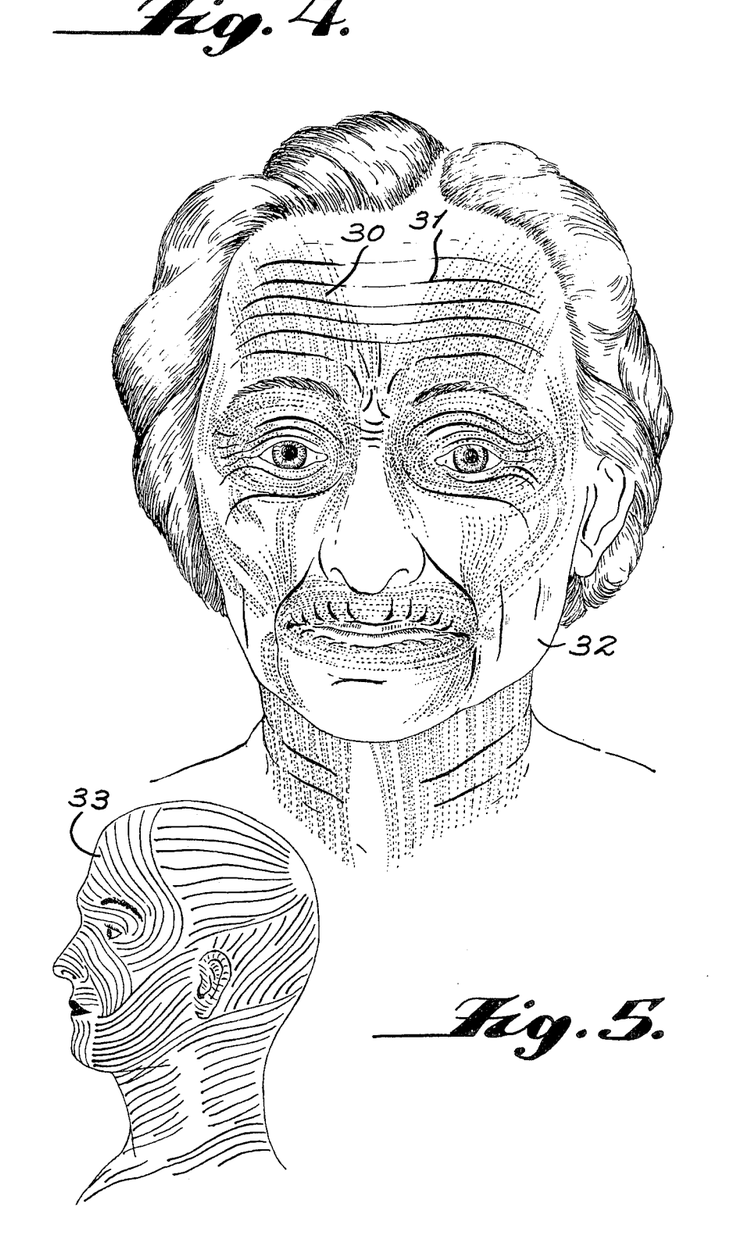
FIG. 4 is a front view of the human face showing the underlying arrangement of muscles and typical wrinkle lines or creases in relation to these.
FIG. 5 is a view of a human head and neck showing Langer's skin tension lines.
Figure 6:
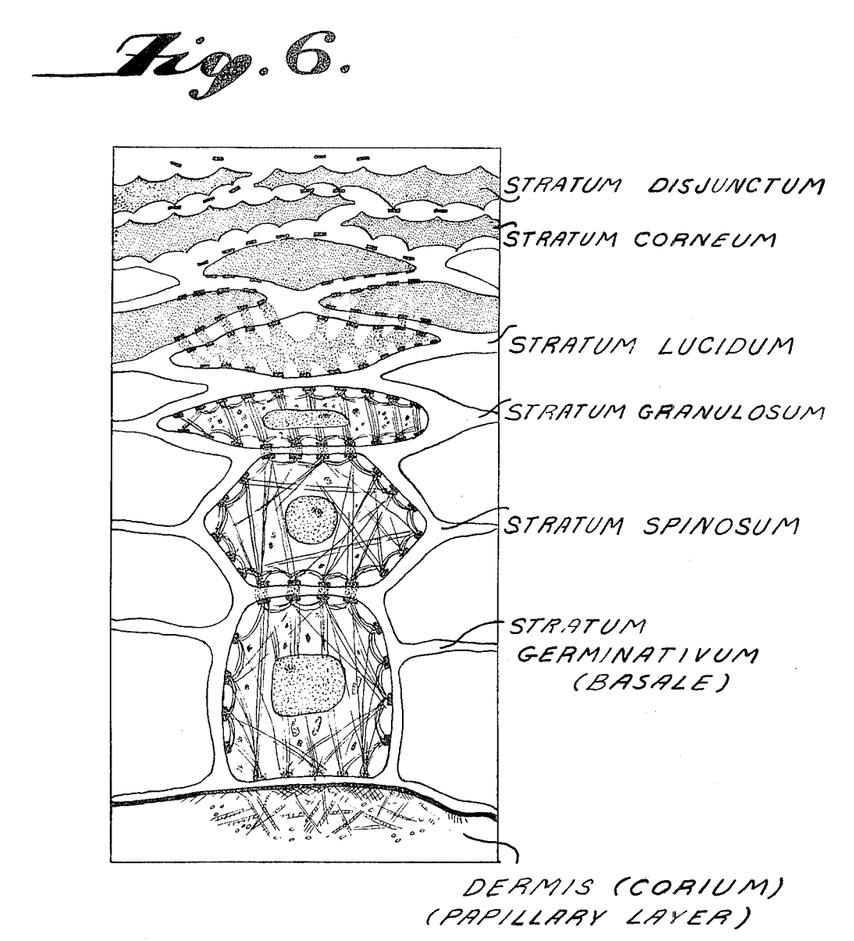
FIG. 6 is a sectional view of the epidermis and dermis showing the shapes and progression of cells and connective tissue and the morphological differentiation of the cells as they progress outwardly.

In regard to the foregoing, FIG. 4 shows the relationship of muscles 30 to wrinkles 31 in a human face 32, as discussed above. The wrinkles that develop at right angles to the longitudinal axes of the muscles and those that develop along Langer's lines 33 (FIG. 5) are controllable, as explained above by the flattening and smoothening of the skin as cells renew the outer skin layer. This latter process of cell movement through the skin is illustrated in FIG. 6.

While the chemical nature of the appliance, including the film and the adhesive, is not critical and may be chosen from a wide range of chemical polymers and copolymers, it is important that at least the adhesive, and most preferably, also the film, be hypoallergenic. Otherwise, as can be easily appreciated, skin rashes and the like can result from continued application of the appliance. Hypoallergenic adhesives and films are known to the art, and are conventionally used in making surgical tapes and the like. Most often, hypoallergenic films will be made of relatively high polymers or copolymers, without any stabilizers, antioxidants or the like therein. Also, the film will normally be homogenous in nature, i.e., not having mobile components thereof, such as plasticizers, e.g., plasticized polyvinyl chloride. Also, in order to provide the desired physical properties of a film, as discussed above, it will normally be required that special kinds of polymeric films be used, especially oriented films (either uniaxially or biaxially oriented films, preferably the latter). If the polymeric material of the film does not have the requisite moisture transmission properties, then the film must be produced in a manner to provide those moisture transmission properties. Methods of producing films of this nature are well known in the art. Basically, moisture transmission properties of the required nature can be provided by minute pores resulting from leeching of solid materials dispersed in the film, or by perforation by a plurality of very small needles, or by pressing and heating of an opencell foamed material to produce the thin film. Other similar methods are well known in the art and need not be detailed in this specification. Polymeric materials suitable for producing the films include polyolefins, such as polyethylene and polypropylene, polyamides, such as nylon 6 and 66, polycarbonates, polysulfones, polyesters, such as those based on polyethyleneterephthalate, polyacetals, polyurethanes and polysilicones.

Similarly, the chemical nature of the adhesive is not critical, so long as the adhesive is hypoallergenic and here again, adhesives of this nature are well known to the art, particularly in connection with surgical tapes. It is only necessary that the adhesives have the properties described above. However, as examples, the adhesive may be chosen from acrylates, polyvinyl alcohol/acetate, silicones, poly (vinyl ethers) isocyanates and cyanoacrylates.

With films and adhesives of the above-described nature, the film normally will have a thickness of at least 4 to 4½ mils and a maximum thickness of between 7 and 10 mils. The adhesive will have a thickness such that the ratio of thickness of the film to the adhesive is between 1:0.25 to 1:0.75. Generally speaking, the adhesive will be between about 1½ and 4 mils, more particularly, between about 2 and 3 mils.

Conveniently, the adhesive will have a releasable film or paper thereon to protect the adhesive; the film or paper is stripped from the adhesive just prior to use of the appliance. The releasable film or paper may be relatively inert polymeric material, such as polyethylene or polypropylene or such coated on a paper. This is conventional in the art as a backing strip for the adhesive and no further details are required.

As a further feature of the invention, the adhesive may contain additional ingredients which promote the desired result of removing wrinkles. Other ingredients, for related purposes, may also be contained in the adhesive. Thus, conventional bactericides, fungicides and the like may be incorporated into the adhesive to prevent bacterial and fungal growth from taking place under the appliance, although this will not normally be a problem. Additionally, the adhesive may contain a small amount of mild leechable acids which promote the sloughing off of dead cells on the outer layer of the skin. The art recognizes that mild acids can promote dislodging of the dead skin cells from the surface of the skin and these acids can be usefully incorporated into the adhesive. The acids, generally speaking, should not produce a pH on the skin more acid than about 4 and more preferably the pH should not be more acid than 4.5. Further, the acids can contain conventional buffering agents to insure that the pH on the skin is at or above the minimum levels. This is particularly true when inorganic acids are used or when the acid, per se, is a rather strong acid and must be maintained at rather dilute concentration to accomplish the desired result. Thus, for example, hydrochloric acid, a very strong acid, may be used for this purpose in dilute solutions when buffered appropriately with acetic acid and sodium acetate. Alternately, very mild acids, such as acetic acids, crotonic acids, carbonic acids, butyric acids and the like, may be used. Preferably, however, the acid will have an ionization constant $K_a$, which is no greater than $1 \times 10^{-4}$ and more preferably, no greater than $1 \times 10^{-5}$. More often, the ionization constant will be between about $1 \times 10^{-5}$ and $2 \times 10^{-5}$. However, even weaker acids may be used, such as carbonic acids, noted above. For purposes of the present specification, the term "acid" is used in its broadest sense to include acid-like materials, such as phenol which acts as thought it were an acid. The effect of the acid is to promote sloughing off of the dead skin cells and, therefore, does constitute an important feature of the invention.

The adhesive may also contain conventional skin-sloughing ingredients, such as humectants, e.g., higher alcohols, softeners, such as sperm oil, and the like.

The amount of the additional ingredients in the adhesive can be chosen as desired and these amounts are not critical, so long as the additional ingredients do not interfere with the adhesive properties of the adhesive and so long as the amounts of the acid keep the pH of the adhesive within the above-noted ranges.

As an example of a specific case which has been found to be most useful in connection with the present invention, the film will be commercially available 4.8 mil polyethylene/ethylene vinyl acetate copolymer. The adhesive will be commercially available acrylic copolymer adhesive and the adhesive can be protected with commercially available silicone/polyethylene-coated paper. The appliance will transmit about 2 to 3 grams of water per square inch during 24 hours of time. The adhesion will be about 20 ounces per inch. The tensile strength will be about 6–7 pounds per inch. The elongation will be about 75%. The thickness of the adhesive will be about 2–3 mils. The porosity will be about 2.8 seconds/maximum.

In the foregoing regards and in connection with the definitions in the specification and claims, the adhesion is measured by Federal Test Method 147C-10.2. The tensile strength is measured by Federal Test Method 147C-34.2. The elongation is measured by Federal Test Method 147C-34.2. The thickness of the appliance, including the film and the adhesive, is measured by Federal Test Method 147C-36.2. The porosity is measured by ASTM Method D 726-59-A. Thus, the units and definitions above are in accordance with the forenoted test methods and descriptions.

What is claimed is:

1. A method for reducing facial wrinkles comprising:
    1. tightly applying to wrinkle prone areas of the human face a pressure-sensitive adhesive appliance in such a manner that the skin under the appliance is placed in a flattened and smoothed configuration;
    2. allowing the appliance to remain in place for at least four hours;
    3. removing the appliance and thereby strip therewith dead skin cells from the surface of the skin; and
    4. repeating steps 1, 2 and 3 a plurality of times with no more than 48 hours elapsing between a repetition thereof and said repetition being continued for at least 15 days;

and wherein the said appliance is capable of transmitting an amount of moisture at least equal to the moisture transmitted by the normal facial skin of a human at rest and wherein the appliance is comprised of a film and a pressure-sensitive adhesive coating thereon, said film having a tensile strength of at least 3 pounds per inch, and an ultimate elongation of between 20 and 150%, said pressure-sensitive adhesive providing an adhesion of between 5 and 50 ounces per inch between the adhesive and the film and between 2 and 30 ounces per inch between the adhesive and the skin and the adhesion between the adhesive and the film is greater than the adhesion between the adhesive and the skin.

2. The method of claim 1 wherein the appliance remains in place for at least 6 hours.

3. The method of claim 1 wherein steps 1, 2 and 3 are repeated with no more than 36 hours between a repetition.

4. The method of claim 1 wherein the repetition of steps 1, 2 and 3 is continued for at least 30 days.

5. The method of claim 1 wherein the repetition of steps 1, 2 and 3 is continued for at least 60 days.

6. The method of claim 1 wherein the ultimate elongation of the film is between 40 and 100%.

7. The method of claim 1 wherein the film and/or the adhesive is hypoallergenic.

8. The method of claim 1 wherein the film and/or adhesive is a high polymer or copolymer.

9. The method of claim 1 wherein the thickness of the film is between 4 and 10 mils and the thickness of the adhesive is between 1½ and 4 mils.

10. The method of claim 1 wherein the adhesive contains one or more of a bactericide, fungicide, acid or humectant.

11. The method of claim 10 wherein the acid has a $K_a$ value of no greater than $10^{-4}$.

* * * * *